(12) United States Patent
Hodorek et al.

(10) Patent No.: US 10,722,374 B2
(45) Date of Patent: Jul. 28, 2020

(54) CONVERTIBLE GLENOID IMPLANT

(71) Applicant: Tornier, Inc., Bloomington, MN (US)

(72) Inventors: Brian C. Hodorek, Winona Lake, IN (US); Shawn Martin Gargac, Fort Wayne, IN (US)

(73) Assignee: Tornier, Inc., Bloomington, MN (US)

( * ) Notice: Subject to any disclaimer, the term of this patent is extended or adjusted under 35 U.S.C. 154(b) by 11 days.

(21) Appl. No.: 15/058,045

(22) Filed: Mar. 1, 2016

(65) Prior Publication Data

US 2016/0324649 A1 Nov. 10, 2016

Related U.S. Application Data

(60) Provisional application No. 62/157,059, filed on May 5, 2015.

(51) Int. Cl.
*A61F 2/40* (2006.01)
*A61F 2/30* (2006.01)

(52) U.S. Cl.
CPC .. *A61F 2/4081* (2013.01); *A61F 2002/30362* (2013.01); *A61F 2002/30487* (2013.01); *A61F 2002/30563* (2013.01); *A61F 2002/30565* (2013.01); *A61F 2002/30774* (2013.01); *A61F 2002/30878* (2013.01); *A61F 2002/4022* (2013.01); *A61F 2002/4085* (2013.01); *A61F 2220/0008* (2013.01)

(58) Field of Classification Search
CPC ................................ A61F 2/4081; A61F 2/581
See application file for complete search history.

(56) References Cited

U.S. PATENT DOCUMENTS

| 4,725,280 A | 2/1988 | Laure |
| 4,986,833 A | 1/1991 | Worland |

(Continued)

FOREIGN PATENT DOCUMENTS

| DE | 10123517 C1 | 11/2002 |
| EP | 0581667 | 2/1994 |

(Continued)

OTHER PUBLICATIONS

Extended European Search Report for EP Appl. No. 16161842.6 dated Sep. 30, 2016 in 7 pages.

(Continued)

*Primary Examiner* — Bruce E Snow
*Assistant Examiner* — Melissa A Hoban
(74) *Attorney, Agent, or Firm* — Knobbe, Martens, Olson & Bear, LLP

(57) ABSTRACT

A glenoid implant including a base plate and an articular component. The base plate can include a body and a support structure extending from a distal surface of the body. The body can include a plurality of openings. The articular component can be configured to removably couple to the base plate. The articular component can include a recessed portion configured to at least partially receive the body of the base plate. At least one engagement structure can protrude from a distal facing surface of the recessed portion. Each engagement structure can correspond to one of the plurality of openings in the body. A distal face of the articular component surrounding the recessed portion can be configured to abut the subchondral bone.

17 Claims, 14 Drawing Sheets

(56) References Cited

U.S. PATENT DOCUMENTS

| | | | |
|---|---|---|---|
| 5,032,132 A | 7/1991 | Matsen, III et al. | |
| 5,033,036 A | 7/1991 | Ohmori et al. | |
| 5,080,673 A | 1/1992 | Burkhead et al. | |
| 5,108,446 A | 4/1992 | Wagner et al. | |
| 5,458,637 A | 10/1995 | Hayes | |
| 5,489,309 A | 2/1996 | Lackey et al. | |
| 5,489,311 A | 2/1996 | Cipolletti | |
| 5,531,973 A | 7/1996 | Sarv | |
| 5,662,657 A | 9/1997 | Carn | |
| 5,702,447 A | 12/1997 | Walch et al. | |
| 5,800,551 A | 9/1998 | Williamson et al. | |
| 5,954,722 A | 9/1999 | Bono | |
| 6,102,954 A | 8/2000 | Albrektsson et al. | |
| 6,171,342 B1 | 1/2001 | O'Neil et al. | |
| 6,228,119 B1 | 5/2001 | Ondrla et al. | |
| 6,228,120 B1 | 5/2001 | Leonard et al. | |
| 6,406,495 B1 | 6/2002 | Schoch | |
| 6,508,841 B2 | 1/2003 | Martin et al. | |
| 6,514,287 B2 | 2/2003 | Ondrla et al. | |
| 6,673,115 B2 | 1/2004 | Resch et al. | |
| 6,679,916 B1* | 1/2004 | Frankle | A61F 2/4081 623/19.12 |
| 6,699,289 B2* | 3/2004 | Iannotti | A61B 17/1684 623/19.11 |
| 6,761,740 B2 | 7/2004 | Tornier | |
| 6,783,549 B1 | 8/2004 | Stone et al. | |
| 6,790,234 B1 | 9/2004 | Frankle | |
| 6,860,903 B2 | 3/2005 | Mears et al. | |
| 6,911,047 B2 | 6/2005 | Rockwood, Jr. et al. | |
| 6,953,478 B2* | 10/2005 | Bouttens | A61F 2/4081 623/19.11 |
| 6,969,406 B2 | 11/2005 | Tornier | |
| 7,160,328 B2 | 1/2007 | Rockwood, Jr. et al. | |
| 7,169,184 B2 | 1/2007 | Pria | |
| 7,175,663 B1* | 2/2007 | Stone | A61F 2/40 623/19.13 |
| 7,175,665 B2 | 2/2007 | German et al. | |
| 7,204,854 B2 | 4/2007 | Guederian et al. | |
| 7,316,715 B2 | 1/2008 | Plaskon | |
| 7,462,197 B2* | 12/2008 | Tornier | A61F 2/4081 623/19.11 |
| 7,462,199 B2 | 12/2008 | Justin et al. | |
| 7,604,665 B2 | 10/2009 | Iannotti et al. | |
| 7,608,109 B2 | 10/2009 | Dall Pria | |
| 7,611,539 B2 | 11/2009 | Bouttens et al. | |
| 7,621,961 B2 | 11/2009 | Stone | |
| 7,637,928 B2 | 12/2009 | Fernandez | |
| 7,648,530 B2 | 1/2010 | Habermeyer et al. | |
| 7,666,522 B2 | 2/2010 | Justin et al. | |
| 7,753,959 B2 | 7/2010 | Berelsman et al. | |
| 7,766,969 B2 | 8/2010 | Justin et al. | |
| 7,854,768 B2 | 12/2010 | Wiley et al. | |
| 7,892,287 B2 | 2/2011 | Deffenbaugh | |
| 7,922,769 B2 | 4/2011 | Deffenbaugh et al. | |
| 7,927,335 B2 | 4/2011 | Deffenbaugh et al. | |
| 7,993,408 B2 | 8/2011 | Meridew et al. | |
| 8,007,523 B2 | 8/2011 | Wagner et al. | |
| 8,048,161 B2 | 11/2011 | Guederian et al. | |
| 8,062,376 B2 | 11/2011 | Shultz et al. | |
| 8,070,820 B2 | 12/2011 | Winslow et al. | |
| 8,092,545 B2 | 1/2012 | Coon et al. | |
| 8,206,453 B2* | 6/2012 | Cooney, III | A61F 2/4684 623/21.12 |
| 8,231,683 B2 | 7/2012 | Lappin et al. | |
| 8,241,365 B2 | 8/2012 | Williams, Jr. et al. | |
| 8,287,600 B2 | 10/2012 | Angibaud | |
| 8,308,807 B2 | 11/2012 | Seebeck et al. | |
| 8,357,201 B2 | 1/2013 | Mayer et al. | |
| 8,361,157 B2 | 1/2013 | Bouttens et al. | |
| 8,425,614 B2 | 4/2013 | Winslow et al. | |
| 8,444,680 B2 | 5/2013 | Dooney, Jr. et al. | |
| 8,449,617 B1 | 5/2013 | McDaniel et al. | |
| 8,454,702 B2 | 6/2013 | Smits et al. | |
| 8,465,548 B2 | 6/2013 | Long | |
| 8,480,750 B2 | 7/2013 | Long | |
| 8,532,806 B1 | 9/2013 | Masson | |
| 8,556,902 B2 | 10/2013 | Ek et al. | |
| 8,556,980 B2 | 10/2013 | Deffenbaugh | |
| 8,556,981 B2 | 10/2013 | Jones et al. | |
| 8,591,591 B2 | 11/2013 | Winslow et al. | |
| 8,597,334 B2 | 12/2013 | Mocanu | |
| 8,632,597 B2 | 1/2014 | Lappin | |
| 8,690,951 B2 | 4/2014 | Baum et al. | |
| 8,753,402 B2 | 6/2014 | Winslow et al. | |
| 8,790,402 B2 | 7/2014 | Monaghan et al. | |
| 8,840,676 B2 | 9/2014 | Belew | |
| 8,961,611 B2 | 2/2015 | Long | |
| 9,114,017 B2 | 8/2015 | Lappin | |
| 9,233,003 B2 | 6/2016 | Roche et al. | |
| 9,498,345 B2 | 11/2016 | Burkhead et al. | |
| 9,629,725 B2 | 4/2017 | Gargac et al. | |
| 10,034,757 B2 | 7/2018 | Kovacs et al. | |
| 10,064,734 B2 | 9/2018 | Burkhead, Jr. et al. | |
| 10,251,755 B2 | 4/2019 | Boileau et al. | |
| 10,357,373 B2 | 7/2019 | Gargac et al. | |
| 2001/0037153 A1 | 11/2001 | Rockwood et al. | |
| 2002/0095214 A1 | 7/2002 | Hyde, Jr. | |
| 2003/0055507 A1 | 3/2003 | McDevitt et al. | |
| 2003/0149485 A1 | 8/2003 | Tornier | |
| 2004/0030394 A1 | 2/2004 | Horber | |
| 2004/0059424 A1 | 3/2004 | Guederian et al. | |
| 2004/0106928 A1 | 6/2004 | Ek | |
| 2004/0220673 A1 | 11/2004 | Pria | |
| 2004/0220674 A1 | 11/2004 | Pria | |
| 2005/0049709 A1 | 3/2005 | Tornier | |
| 2005/0060039 A1 | 3/2005 | Cyprien | |
| 2005/0143831 A1 | 6/2005 | Justin et al. | |
| 2005/0149044 A1 | 7/2005 | Justin et al. | |
| 2005/0261775 A1* | 11/2005 | Baum | A61F 2/4081 623/19.12 |
| 2005/0278030 A1* | 12/2005 | Tornier | A61F 2/30734 623/19.11 |
| 2006/0074353 A1 | 4/2006 | Deffenbaugh et al. | |
| 2006/0100714 A1 | 5/2006 | Ensign | |
| 2006/0122705 A1 | 6/2006 | Morgan | |
| 2006/0142865 A1 | 6/2006 | Hyde, Jr. | |
| 2006/0200248 A1 | 9/2006 | Beguin et al. | |
| 2006/0200249 A1 | 9/2006 | Beguin et al. | |
| 2007/0016304 A1 | 1/2007 | Chudik | |
| 2007/0055380 A1 | 3/2007 | Berelsman et al. | |
| 2007/0100458 A1 | 5/2007 | Dalla Pria | |
| 2007/0142921 A1 | 6/2007 | Lewis et al. | |
| 2007/0156246 A1 | 7/2007 | Meswania et al. | |
| 2007/0179624 A1 | 8/2007 | Stone et al. | |
| 2007/0219638 A1* | 9/2007 | Jones | A61F 2/4081 623/19.11 |
| 2007/0244563 A1* | 10/2007 | Roche | A61F 2/40 623/19.12 |
| 2007/0244564 A1 | 10/2007 | Ferrand et al. | |
| 2008/0183297 A1* | 7/2008 | Boileau | A61B 17/1635 623/19.14 |
| 2008/0269906 A1 | 10/2008 | Iannotti et al. | |
| 2008/0294268 A1 | 11/2008 | Baum et al. | |
| 2008/0306601 A1 | 12/2008 | Dreyfuss | |
| 2009/0125113 A1 | 5/2009 | Guederian et al. | |
| 2009/0149961 A1* | 6/2009 | Dallmann | A61F 2/4003 623/19.11 |
| 2009/0204225 A1 | 8/2009 | Meridew et al. | |
| 2009/0216332 A1* | 8/2009 | Splieth | A61F 2/4684 623/19.14 |
| 2009/0281630 A1 | 11/2009 | Delince et al. | |
| 2009/0292364 A1 | 11/2009 | Linares | |
| 2010/0016975 A1 | 1/2010 | Iannotti et al. | |
| 2010/0023068 A1 | 1/2010 | Bouttens et al. | |
| 2010/0049327 A1 | 2/2010 | Isch et al. | |
| 2010/0087927 A1 | 4/2010 | Roche et al. | |
| 2010/0161066 A1 | 6/2010 | Iannotti et al. | |
| 2010/0217399 A1 | 8/2010 | Groh | |
| 2010/0234959 A1 | 9/2010 | Roche et al. | |
| 2010/0274359 A1* | 10/2010 | Brunnarius | A61F 2/30734 623/19.13 |
| 2010/0291401 A1 | 11/2010 | Medina et al. | |

(56) References Cited

U.S. PATENT DOCUMENTS

| | | | |
|---|---|---|---|
| 2010/0331990 A1* | 12/2010 | Mroczkowski | A61F 2/4081 623/19.11 |
| 2011/0035013 A1 | 2/2011 | Winslow et al. | |
| 2011/0118846 A1* | 5/2011 | Katrana | A61F 2/4014 623/19.13 |
| 2011/0144760 A1 | 6/2011 | Wong et al. | |
| 2011/0190899 A1 | 8/2011 | Pierce et al. | |
| 2011/0282393 A1 | 11/2011 | Garlach et al. | |
| 2012/0004733 A1* | 1/2012 | Hodorek | A61F 2/40 623/19.11 |
| 2012/0029647 A1 | 2/2012 | Winslow et al. | |
| 2012/0165954 A1 | 6/2012 | Nimal | |
| 2012/0191201 A1* | 7/2012 | Smits | A61F 2/4081 623/19.11 |
| 2012/0209392 A1* | 8/2012 | Angibaud | A61F 2/4014 623/19.11 |
| 2012/0221111 A1 | 8/2012 | Burkhead, Jr. et al. | |
| 2012/0221112 A1 | 8/2012 | Lappin | |
| 2012/0232670 A1 | 9/2012 | Bojarski et al. | |
| 2012/0239156 A1 | 9/2012 | De Wilde et al. | |
| 2012/0253467 A1* | 10/2012 | Frankle | A61F 2/40 623/19.11 |
| 2012/0277880 A1 | 11/2012 | Winslow et al. | |
| 2013/0018483 A1 | 1/2013 | Li et al. | |
| 2013/0053968 A1 | 2/2013 | Nardini et al. | |
| 2013/0096631 A1 | 4/2013 | Leung et al. | |
| 2013/0110470 A1 | 5/2013 | Vanasse et al. | |
| 2013/0144393 A1 | 6/2013 | Mutchler et al. | |
| 2013/0150972 A1 | 6/2013 | Iannotti et al. | |
| 2013/0150973 A1 | 6/2013 | Splieth et al. | |
| 2013/0150975 A1 | 6/2013 | Iannotti et al. | |
| 2013/0226309 A1 | 8/2013 | Daigo et al. | |
| 2013/0231754 A1 | 9/2013 | Daigo et al. | |
| 2013/0253656 A1 | 9/2013 | Long | |
| 2013/0261751 A1 | 10/2013 | Lappin | |
| 2013/0261752 A1 | 10/2013 | Lappin et al. | |
| 2013/0264749 A1 | 10/2013 | Jones et al. | |
| 2013/0282135 A1 | 10/2013 | Sun et al. | |
| 2014/0025173 A1 | 1/2014 | Cardon et al. | |
| 2014/0142711 A1 | 5/2014 | Maroney et al. | |
| 2014/0194995 A1 | 7/2014 | Koka | |
| 2014/0257499 A1 | 9/2014 | Winslow et al. | |
| 2014/0277180 A1 | 9/2014 | Paolino et al. | |
| 2014/0371863 A1 | 12/2014 | Vanasse et al. | |
| 2015/0073424 A1 | 3/2015 | Couture et al. | |
| 2015/0094819 A1 | 4/2015 | Iannotti et al. | |
| 2015/0142122 A1* | 5/2015 | Bickley | A61F 2/4081 623/19.11 |
| 2015/0150688 A1 | 6/2015 | Vanasse et al. | |
| 2015/0272741 A1 | 10/2015 | Taylor et al. | |
| 2015/0305877 A1 | 10/2015 | Gargac et al. | |
| 2016/0166392 A1 | 6/2016 | Vanasse et al. | |
| 2016/0270922 A1 | 9/2016 | Pressacco et al. | |
| 2016/0287401 A1* | 10/2016 | Muir | A61F 2/40 |
| 2016/0310285 A1 | 10/2016 | Kovacs et al. | |
| 2017/0027709 A1 | 2/2017 | Winslow et al. | |
| 2017/0042687 A1 | 2/2017 | Boileau et al. | |
| 2017/0042690 A1 | 2/2017 | Burkhead et al. | |
| 2017/0172764 A1 | 6/2017 | Muir et al. | |
| 2017/0273795 A1 | 9/2017 | Neichel et al. | |
| 2017/0273801 A1 | 9/2017 | Hodorek et al. | |
| 2018/0078377 A1 | 3/2018 | Gargac et al. | |
| 2018/0243102 A1 | 8/2018 | Burkhead, Jr. et al. | |
| 2019/0076261 A1 | 3/2019 | Mutchler et al. | |

FOREIGN PATENT DOCUMENTS

| | | |
|---|---|---|
| EP | 0776636 | 6/1997 |
| EP | 1013246 | 11/1999 |
| EP | 1064890 | 1/2001 |
| EP | 1323395 | 7/2003 |
| EP | 1488764 B1 | 12/2006 |
| EP | 1762201 A1 | 3/2007 |
| EP | 1515758 B1 | 3/2009 |
| EP | 2057970 | 5/2009 |
| EP | 1639966 B1 | 9/2009 |
| EP | 1927328 B1 | 1/2011 |
| EP | 1902689 B1 | 11/2011 |
| EP | 1996125 B1 | 5/2013 |
| EP | 2335655 B1 | 7/2013 |
| EP | 1951161 B1 | 4/2014 |
| EP | 1973498 B1 | 4/2014 |
| EP | 2481376 B1 | 4/2014 |
| EP | 2601912 B1 | 7/2016 |
| FR | 2567019 | 1/1986 |
| FR | 2739151 A1 | 3/1997 |
| FR | 2776506 B1 | 8/2000 |
| FR | 2971144 A1 | 8/2012 |
| FR | 2977791 B1 | 7/2014 |
| WO | WO 2011/073169 | 6/2011 |
| WO | WO 2011/150180 A2 | 12/2011 |
| WO | WO 2015/068035 | 5/2015 |
| WO | WO 2015/103090 | 7/2015 |
| WO | WO 2017/007565 | 1/2017 |

OTHER PUBLICATIONS

International Search Report and Written Opinion issue in PCT Application No. PCT/US2016/036500, dated Mar. 22, 2017, in 18 pages.

Anatomical Shoulder™ Inverse/Reverse System Surgical Technique, Product Brochure, Zimmer, Inc., published 2006, in 32 pages.

Boileau, P., et al., "Cemented polyethylene versus uncemented metal-backed glenoid components in total shoulder arthroplasty: A prospective, double-blind, randomized study," Journal of Shoulder and Elbow Surgery, Jul./Aug. 2002, vol. 11, Issue 4, pp. 351-359.

Boileau, P., et al., "Metal-backed glenoid implant with polyethylene insert is not a viable long-term therapeutic option," Journal of Shoulder and Elbow Surgery, Feb. 2015, pp. 1-10.

Castagna, A., et al., "Mid-term results of a metal-backed glenoid component in total shoulder replacement," The Journal of Bone and Joint Surgery, Oct. 2010, vol. 92-B, No. 10, pp. 1410-1415.

Clement, N.D., et al., "An uncemented metal-backed glenoid component in total shoulder arthroplasty for osteoarthritis: factors affecting survival and outcome," The Japanese Orthopaedic Association, published online Sep. 26, 2012, vol. 18, pp. 22-28.

Kany, J., et al., "A convertible shoulder system: is it useful in total shoulder arthroplasty revisions?" International Orthopaedics, published online Oct. 16, 2014, vol. 39, pp. 299-304.

Katz, D., et al., "New design of a cementless glenoid component in unconstrained shoulder arthroplasty: a prospective medium-term analysis of 143 cases," published online Oct. 27, 2012, vol. 23, pp. 27-34.

Montoya, F., et al., "Midterm results of a total shoulder prosthesis fixed with a cementless glenoid component," Journal of Shoulder and Elbow Surgery, May 2013, vol. 22, Issue 5, pp. 628-635.

SMR Axioma® TT Metal Back Surgical Technique, Product Brochure, Lima Corporate, dated Sep. 2013, in 48 pages.

Taunton, M.J., et al., "Total Shoulder Arthroplasty with a Metal-Backed, Bone-Ingrowth Glenoid Component," The Journal of Bone and Joint Surgery, Oct. 2008, vol. 90-A, Issue 10, pp. 2180-2188.

Teissier, P., et al., "The TESS reverse shoulder arthroplasty without a stem in the treatment of cuff-deficient shoulder conditions: clinical and radiographic results," Journal of Shoulder and Elbow Surgery, Jan. 2015, vol. 24, Issue 1, pp. 45-51.

The Anatomical Shoulder™: A true system approach, Product Brochure, Zimmer UK Ltd, printed 2006, in 6 pages.

Eclipse™ Stemless Shoulder Prosthesis, Surgical Technique Guide, Anthrex GmbH, 2014, in 12 pages.

Epoca Shoulder Arthroplasty System, Synthes, Inc., Apr. 2008, in 4 pages.

Epoca Shoulder Arthroplasty System—Stem and Glenoid Technique Guide, Synthes, Inc., Apr. 2008, in 56 pages.

Univers Revers™ Total Shoulder System, Surgical Technique Guide, Anthrex Inc., Version D, revised Jul. 2, 2015, in 28 pages.

(56) References Cited

OTHER PUBLICATIONS

Arthrex, "Arthrex Releases Univers Revers™ Shoulder Arthroplasty System in the United States—First Surgery Successfully Performed in Chillicothe, OH", Jun. 18, 2013.
BIOMET, "Comprehensive® Reverse Shoulder System", 2013.
DJO Surgical, Reverse® shoulder prosthesis Surgical Technique, Feb. 2008.
Innovative Design Orthopaedics, "Verso® Shoulder Surgical Technique", 2013.
Cementless Fixation Using a Polyethyene Oseo-Integration Peg as Used on the Freeman-Samuelson Knee brochure, produced by Finsbury Instruments Limited London in conjunction with Adrian Tuke Limited, 1982.

\* cited by examiner

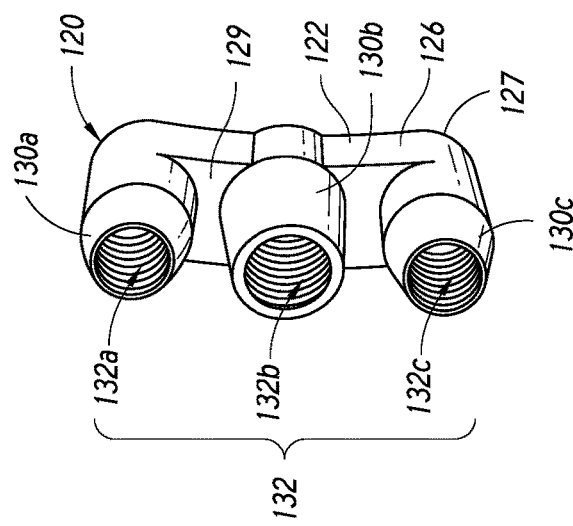
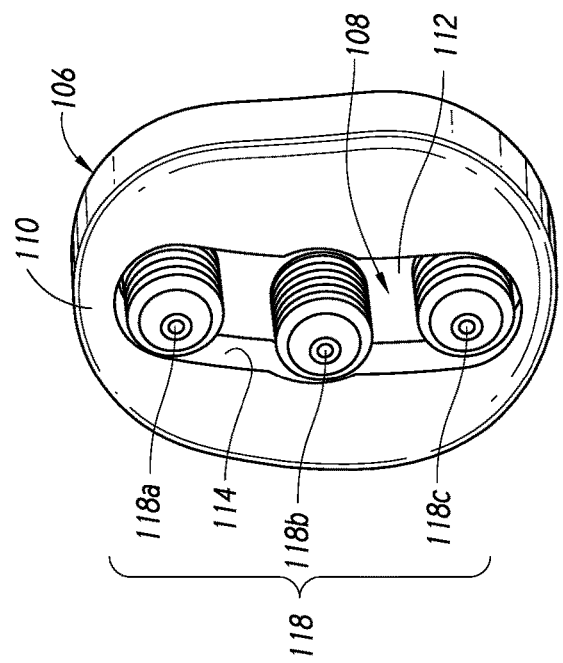
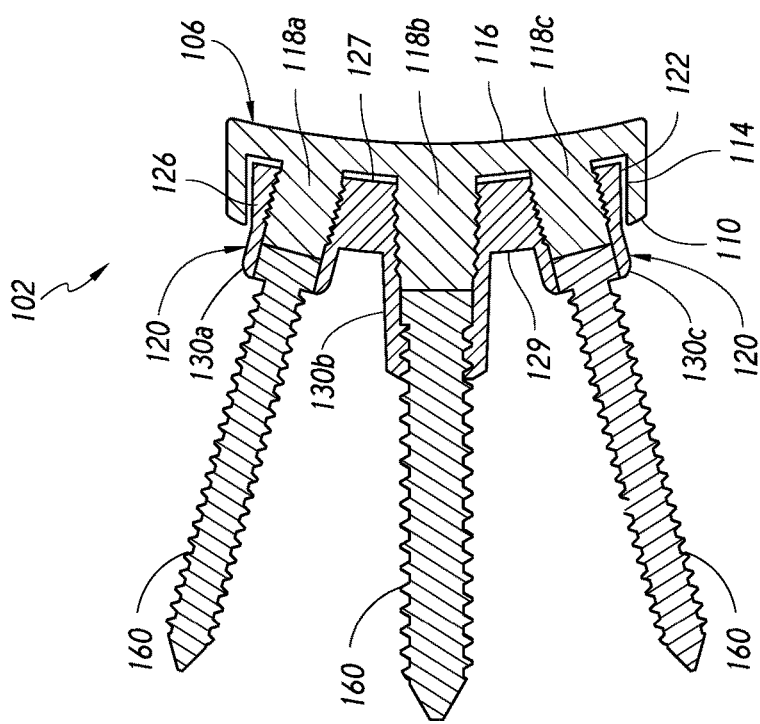
FIG. 4C
FIG. 4B
FIG. 4A

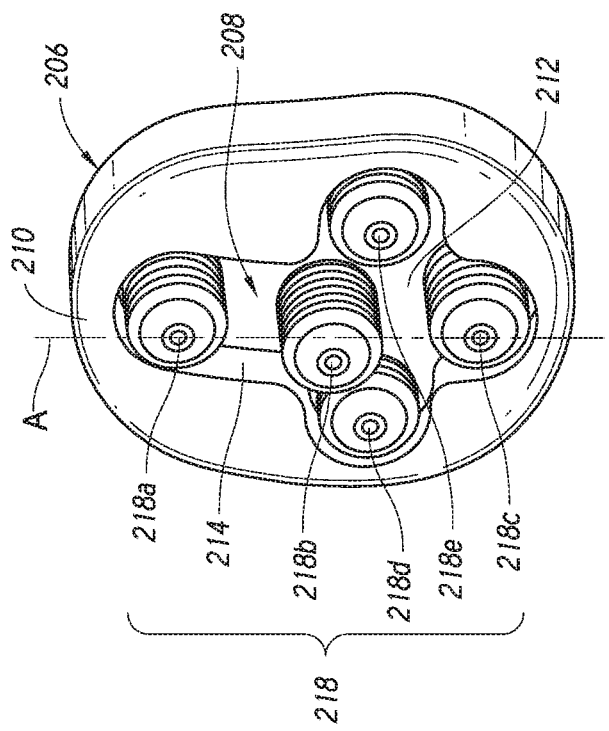
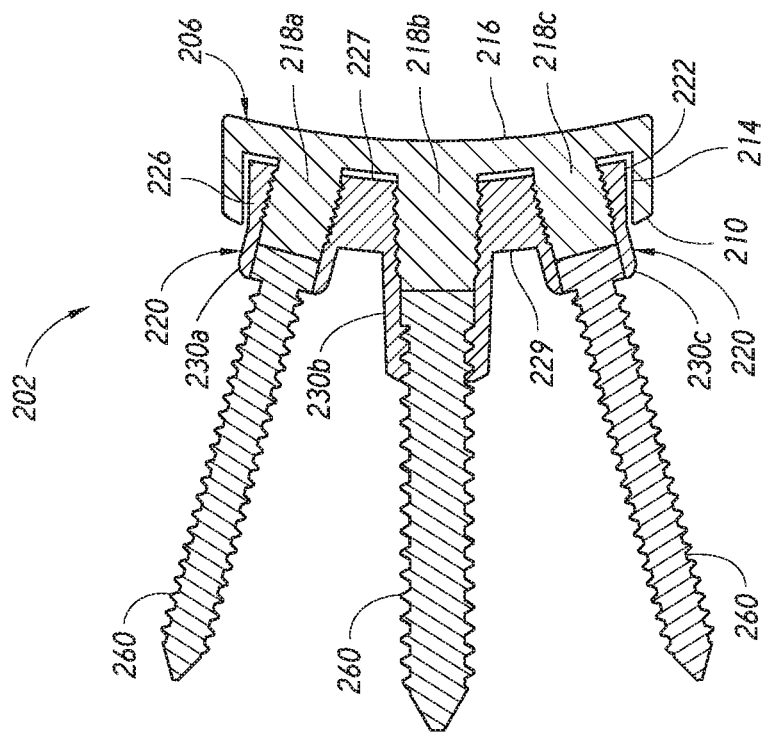

CONVERTIBLE GLENOID IMPLANT

INCORPORATION BY REFERENCE TO ANY PRIORITY APPLICATIONS

This application claims priority benefit under 35 U.S.C. § 119(e) to U.S. Provisional Application No. 62/157,059, filed May 5, 2015, which is hereby incorporated by reference in its entirety herein. Any and all applications for which a foreign or domestic priority claim is identified in the Application Data Sheet as filed with the present application are hereby incorporated by reference under 37 C.F.R. § 1.57.

BACKGROUND

Field

The present disclosure relates to a convertible glenoid implant of a shoulder joint prosthesis.

Description of the Related Art

In a shoulder joint, the head of the humerus interacts with the glenoid cavity of the scapula in a manner similar to a "ball and socket" joint. Over time, it may become necessary to replace the shoulder joint with a prosthetic shoulder joint including a glenoid implant.

The glenoid implant typically includes an articular component that is adapted to articulate with the head of a humeral component, for example, the anatomical head of the humerus or a portion of a humeral implant. In some cases, the glenoid implant may provide an anatomical configuration in which the articular component includes a cavity that replaces the glenoid cavity. In other cases, the glenoid implant may provide a reversed configuration in which the articular component includes a hemispherical dome that cooperates with a complementary cavity defined by a humeral implant.

SUMMARY

Some glenoid implants can include a base plate for fixing the articular body to the glenoid. The base plate can be permanently secured in the glenoid by the surgeon before an articular component is positioned on the base plate. In some cases, the glenoid implant needs to be replaced. The base plate remains coupled to the glenoid and the articular body is replaced. The surgeon may provide a new articular component of a different configuration. For example, the implant may be converted from an anatomical configuration to a reversed configuration.

When the base plate is positioned on the subchondral bone, the combination of the base plate and the articular component (e.g., a glenoid component or a reverse component) can be too thick and further displace the glenoid from the humeral component.

In some cases, a base plate can be at least partially loaded into the glenoid, such that a distal facing surface of the base plate is positioned in the glenoid and beyond the subchondral bone. However, milling the glenoid to insert the base plate can be difficult and require removal of a large portion of the bone. Further, loading the glenoid implant into the glenoid leaves no subchondral bone support behind the base plate. Since there is no subchondral support behind the glenoid implant, surgeons cannot lag screws to achieve the desired compression and the glenoid implant can subside. Thus, it can be desirable for the base plate to be positioned on the subchondral bone to avoid milling the bone. Positioning the base plate on the subchondral bone can also lag the screws into the glenoid to achieve initial fixation.

The base plate may include metal, such as a titanium alloy, while the articular body can include a synthetic material, such as polyethylene. However, the direct interaction between the metal base plate and synthetic articular body can cause the synthetic articular body to wear and displace the articular surface of the glenoid component. Thus, it may be desirable for a proximal surface of the base plate to be spaced apart from a distal facing surface of the articular component when the articular component is coupled to the base plate.

Certain aspects of the disclosure are directed toward a glenoid implant including a base plate and an articular component configured to removably couple to the base plate. The base plate can include a body and a support structure extending from a distal surface of the body. The body can include a plurality of openings. The articular component can include a recessed portion configured to at least partially receive the body of the base plate. At least one engagement structure can protrude from a distal facing surface of the recessed portion. Each engagement structure can correspond to one of the plurality of openings in the body. In certain aspects, a proximal surface of the base plate can be spaced apart from the distal facing surface of the recessed portion when the articular component is coupled to the base plate, and/or a distal face of the articular component surrounding the recessed portion can be configured to abut the subchondral bone.

Certain aspects of the disclosure are directed toward methods of implanting a glenoid implant. The method can include inserting a base plate into a glenoid cavity such that a support structure of the base plate is inserted into a subchondral bone portion and a body of the base plate is positioned thereon a subchondral bone surface. The body can include a plurality of openings. A screw can be advanced through one of the plurality of openings and into the subchondral bone. A first articular component can be secured to the base plate such that a recessed portion of the first articular component is advanced over the body of the base plate and an engagement member of the first articular component is inserted into a corresponding opening of the plurality of openings.

The above-mentioned method can further include removing the first articular component from the base plate and securing a second articular component to the base plate. The first articular component can be a glenoid component and the second articular component can be a reverse component.

Certain aspects of the disclosure are directed toward a glenoid system including a base plate, a glenoid component, and a reverse component. The base plate can include a body and a support structure extending from a distal surface of the body. The body can include a plurality of openings. The glenoid component can be configured to removably couple to the base plate and can include a recessed portion configured to at least partially receive the body of the base plate. A proximal surface of the base plate can be spaced apart from a distal facing surface of the anatomical recessed portion when the glenoid component is coupled to the base plate. The reverse component can be configured to removably couple to the base plate and can include a reverse recessed portion configured to at least partially receive the body of the base plate. The proximal surface of the base plate can be spaced apart from a distal facing surface of the reverse recessed portion when the reverse component is coupled to the base plate.

Any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No individual aspects of this disclosure are essential or indispensable.

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

FIG. 4A illustrates a cross-section of another embodiment of a glenoid implant.

FIG. 4B illustrates a bottom perspective view of the glenoid component shown in FIG. 3A.

FIG. 4C illustrates a bottom perspective view of the base plate shown in FIG. 3B.

FIG. 5A illustrates a cross-section of another embodiment of a glenoid implant.

FIG. 5B illustrates a bottom perspective view of the glenoid component shown in FIG. 4A.

DETAILED DESCRIPTION

Some glenoid implants can include a base component for fixing the articular body to the glenoid. The base component can be permanently secured in the glenoid by the surgeon, for example by using screws, before an articular component is positioned on the base plate. In some cases, the glenoid implant needs to be replaced. The base component remains coupled to the glenoid and the articular body is replaced. The surgeon may provide a new articular component of a different configuration. For example, the implant may be converted from an anatomical configuration to a reversed configuration.

Figure 1:
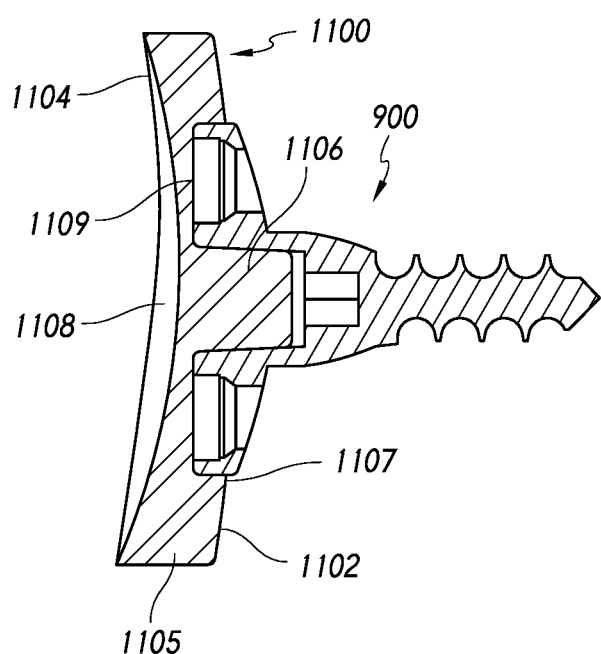
FIG. 1 represents a cross-sectional view of a prior art embodiment of modular glenoid implant.

Glenoid components known in the art have typically been constructed from metal. FIG. 1 illustrates one such example of a glenoid component 1100 having a metal body 1105 and a metal base plate 900. The body 1105 defines circumferential recess 1107, which extends from the medial side 1102 towards the lateral side 1104. The tapered trunnion 1106 extends from the base 1109 of recess 1107 towards the medial side 1102, tapers from base 1009 to its proximal end, and is adapted to be received and attached to the tapered cavity 910 of the baseplate 900. Recess 1107 is adapted to receive a portion, or the entirety of, the body 902 of the baseplate 900.

Single Engagement Structure

FIGS. 2A-2F illustrate glenoid implants 2, 1002 that can been implanted in a glenoid. Each of the glenoid implants 2, 1002 can include an articular component (e.g., a glenoid component 6 or a reverse component 40) removably secured to a base plate 20. For example, the glenoid implant 2 can include a glenoid component 6 configured to be removably coupled to the base plate 20 (see FIGS. 2A and 2B).

Figure 2B:
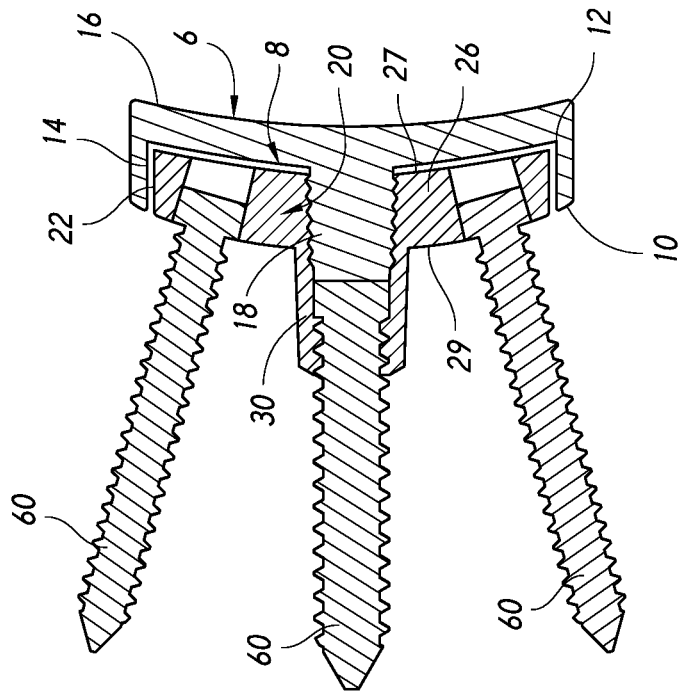
FIG. 2B illustrates a cross-section of the glenoid implant shown in FIG. 2A taken along line 2B-2B.
Figure 2A:
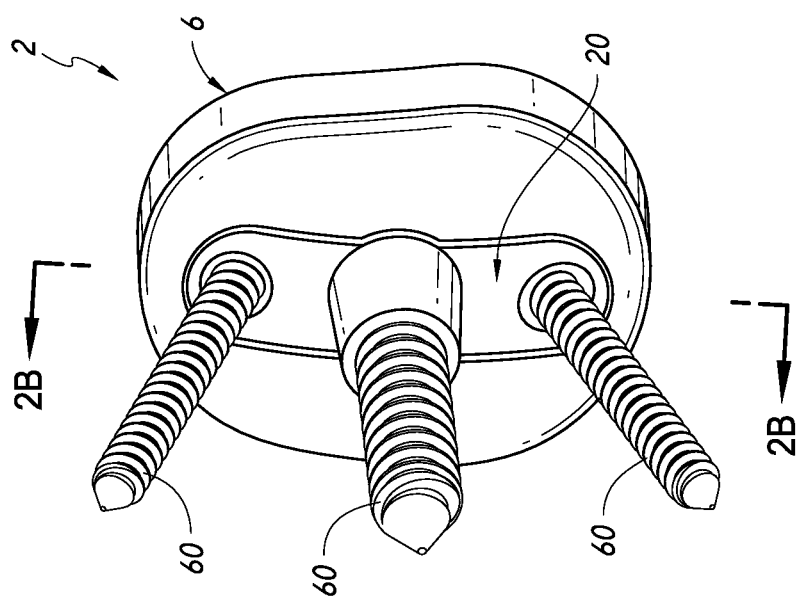
FIG. 2A illustrates a bottom perspective view of an embodiment of a glenoid implant.
Figure 2C:
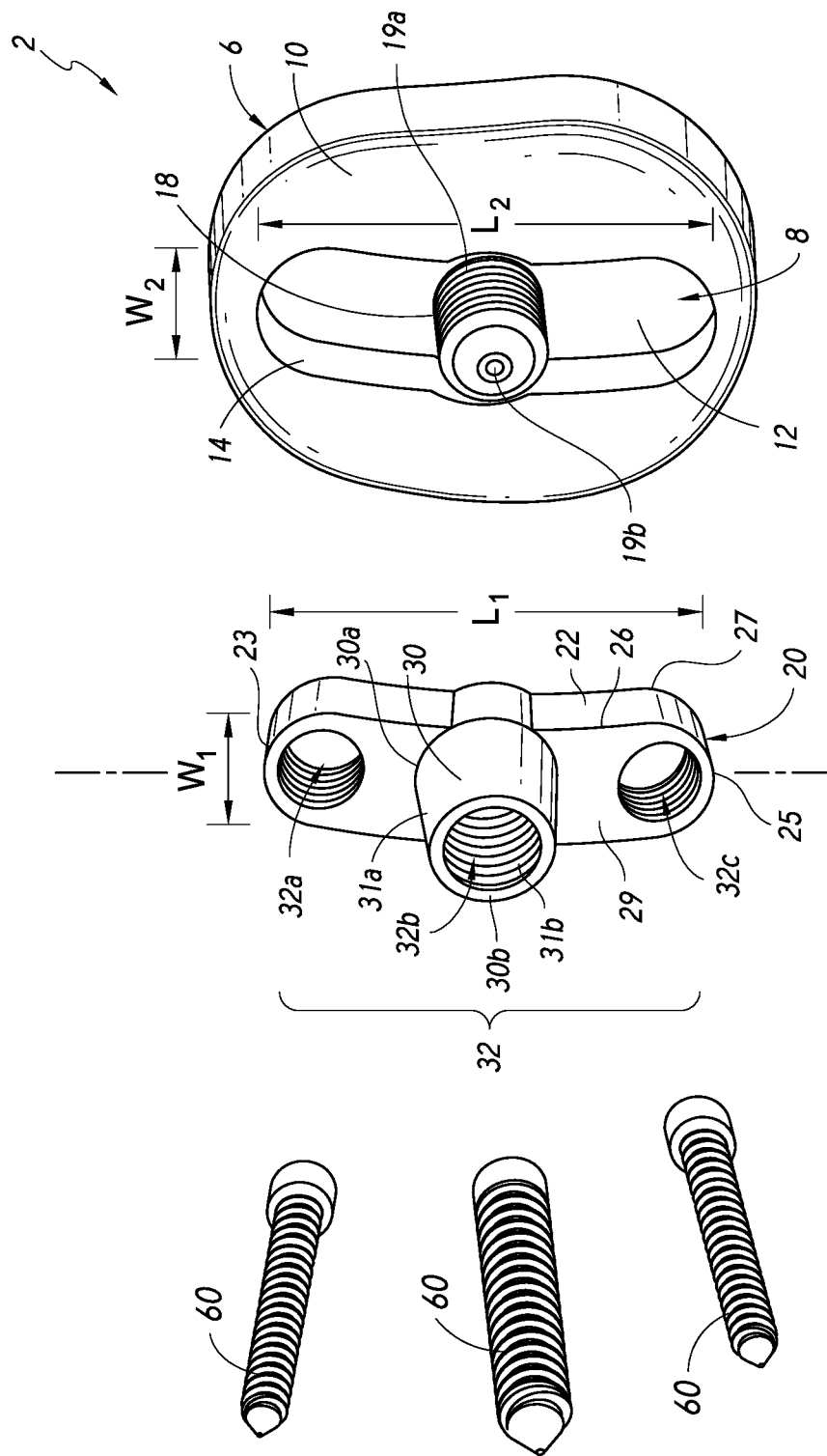
FIG. 2C illustrates an exploded view of the glenoid implant shown in FIG. 2A.

As shown in FIG. 2C, the base plate 20 can include a body 26 and a support structure 30. The body 26 can include an outer peripheral wall 22 having generally curved and/or flat surfaces. The outer peripheral wall 22 can extend between a lateral surface 27 (or proximal face) and a medial surface 29 (or distal face) of the body 26 (see FIG. 2C). A thickness of the body 26 can be defined from the lateral surface 27 to the medial surface 29 of the body 26. A length $L_1$ of the body 26 can be defined from a superior edge 23 of the body 26 to an inferior edge 25 of the body 26 (see FIG. 2C) and extend along an axis generally perpendicular to a longitudinal axis of the glenoid implant 2 when the implant 2 is secured to the glenoid (see FIGS. 3A and 3B). A width $W_1$ of the body 26 can be measured perpendicular to the length $L_1$.

The body 26 can be generally elongate. For example, the body 26 can be generally rectangular, generally elliptical, or any other elongate shape. A length $L_1$ of the body 26 can be substantially longer than a width $W_1$ of the body 26, e.g., the length $L_1$ can be at least about three times longer than the width $W_1$, at least about four times longer than the width $W_1$, or more (see FIG. 2C).

The body 26 can include a plurality of openings 32 (e.g., two, three, four, five, or more). At least some or all of the plurality of openings 32 can be aligned along the length $L_1$ of the body 26. For example, as shown in FIG. 2C, the body 26 can include three openings 32a, 32b, 32c aligned along the length $L_1$ of the body 26. One or more of the openings 32 may be threaded on an internal wall thereof and adapted to engage a screw 60 (e.g., having a single lead, double lead, triple lead, or other number of leads and/or right or left-handed threads).

The support structure 30 can extend from the medial surface 29 of the body 26 and extend generally perpendicular to the body 26 (see FIG. 2C). The support structure 30 can include a circumferential wall portion extending from a proximal portion 30a to a distal portion 30b of the support structure 30. The wall portion can include an exterior surface 31a and an interior surface 31b defining a lumen extending through the support structure 30. The exterior surface 31a can be generally smooth and without any threads, ribs, grooves, or other structures. The interior surface 31b can be threaded and adapted to engage a screw 60 and/or an engagement structure 18 of the glenoid component 6.

The lumen of the support structure 30 can be aligned with one of the openings 32. In some instances, as shown in FIG. 2C, the opening 32b aligned with the lumen of the support structure 30 can have a larger diameter than the peripheral openings 32a, 32c. Accordingly, a larger screw 60 can be advanced through the support structure opening 32b than the peripheral openings 32a, 32c.

As shown in FIG. 2C, the support structure 30 can taper from the proximal portion 30a toward the distal portion 30b. For example, the support structure 30 can be generally frustoconical and/or include a chamfer edge at the distal portion 30b of the support structure 30. In certain variants, the support structure 30 can be generally cylindrical and include a generally uniform diameter.

FIG. 2C also illustrates an embodiment of the glenoid component 6 adapted to engage the base plate 20. The glenoid component 6 can include a lateral surface 16 (or proximal face) and a medial surface 10 (or distal face). The medial surface 10 can have a recessed portion 8 with a peripheral wall 14 and a medial-facing surface 12 (or distal-facing surface). The recessed portion 8 can be shaped and sized to receive at least a partial thickness of the body 26. More particularly, when assembled, the lateral surface 27 of the base plate 8 can be positioned adjacent to and spaced away from the medial-facing surface 12 of the recessed portion 8.

The recessed portion 8 can have generally the same shape as the body 26 such that the recessed portion can at least partially or entirely receive the body 26 therein. For instance, the recessed portion 8 can have a generally elongate shape. A length $L_2$ of the recessed portion 8 can be substantially longer than a width $W_2$ of the body 26, e.g., the length $L_2$ can be at least about three times longer than the width $W_2$, at least about four times longer than the width $W_2$, or more. In embodiments, the shape of the recessed portion 8 is complementary to the body 26, such that the recessed portion is shaped to receive the body 26 therein. The recessed portion 8 can be centrally located with respect to the glenoid component 6.

The length $L_2$ and/or width $W_2$ of the recessed portion 8 can be greater than the length $L_1$ and/or width $W_1$ of the body 26, respectively (see FIG. 2C), such that a space remains between the peripheral walls 14 of the recessed portion 8 and the outer peripheral wall 22 of the body 26 when the glenoid implant 2 is fully assembled (see FIG. 2B). A thickness of the peripheral wall 14 of the recessed portion 8 can be greater than a thickness of the peripheral wall 22 the body 26, such that when the glenoid implant 2 is fully assembled, a space remains between the lateral surface 27 of the body 26 and the medial-facing surface 12 of the recessed portion 8. When the implant 2 is fully assembled, the medial surface 29 of the body 26 can be aligned or flush with the medial surface 10 of the glenoid component 6.

The spacing between the recessed portion 8 and the body 26 can prevent wear between the glenoid component 6 and the base plate 20, particularly when the base plate 20 comprises a metal (e.g., a titanium alloy) and when the glenoid component 6 comprises a polymer (e.g., polyethylene). Although not shown, the space between the recessed portion 8 and the body 26 can be filled with a shock absorbing material, such as polymers and copolymers, including, but not limited to silicones and polyurethanes.

At least one engagement structure 18 (e.g., one, two, three, four, five or more engagement structures) can extend from the medial-facing surface 12 of the recessed portion 8 and extend generally perpendicular to the length $L_2$ of the recessed portion 8. Each engagement structure 18 can be a peg, a barb, a screw, or other protruding structure, configured to be received by one of the openings 32 of the body 26 by a screw fit, snap fit, interference fit, or otherwise. As shown in FIG. 2C, the glenoid component 6 can include a single engagement structure 18 configured to interface with the opening 32b and/or the support structure 30.

Each engagement structure 18 can include an outer wall portion that can be threaded to threadably engage of the openings 32. The outer wall portion can extend from a proximal portion 19a to a distal portion 19b of the engagement structure 18. A length of the engagement structure 18 can be greater than a thickness of the recessed portion 8, such that the distal portion 19b of the engagement structure 18 extends distally of the medial surface 10 of the glenoid component 6. The distal portion 19b of the engagement structure 18 can be tapered to facilitate insertion of the engagement structure 18 into one of the openings 32 and/or the support structure 30.

Figure 2E:
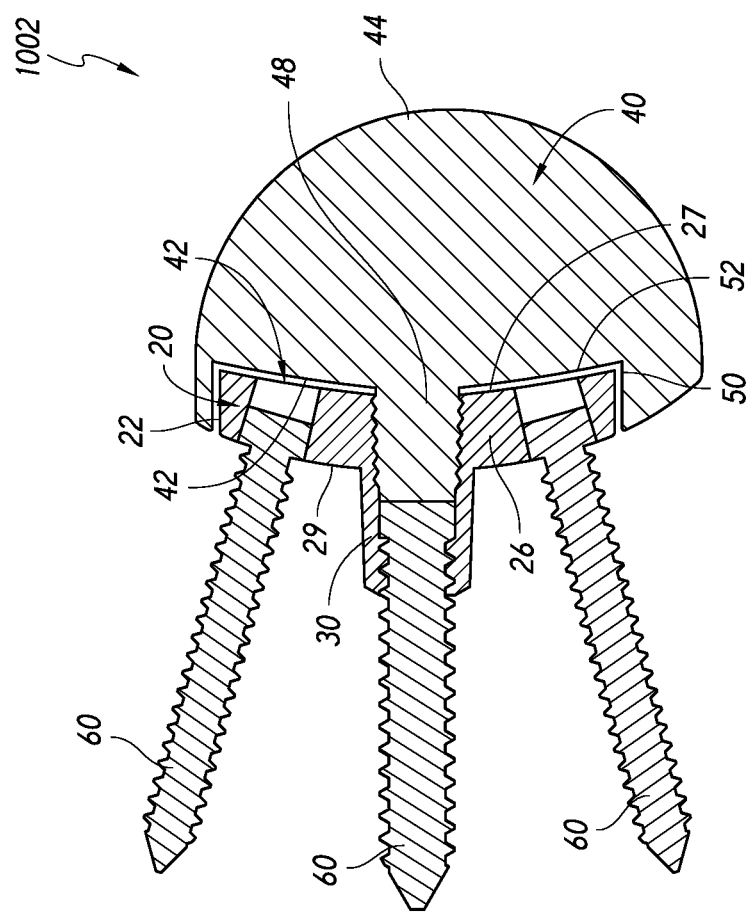
FIG. 2E illustrates a cross-section of an embodiment of a glenoid implant including the reverse component shown in FIG. 2D.
Figure 2D:
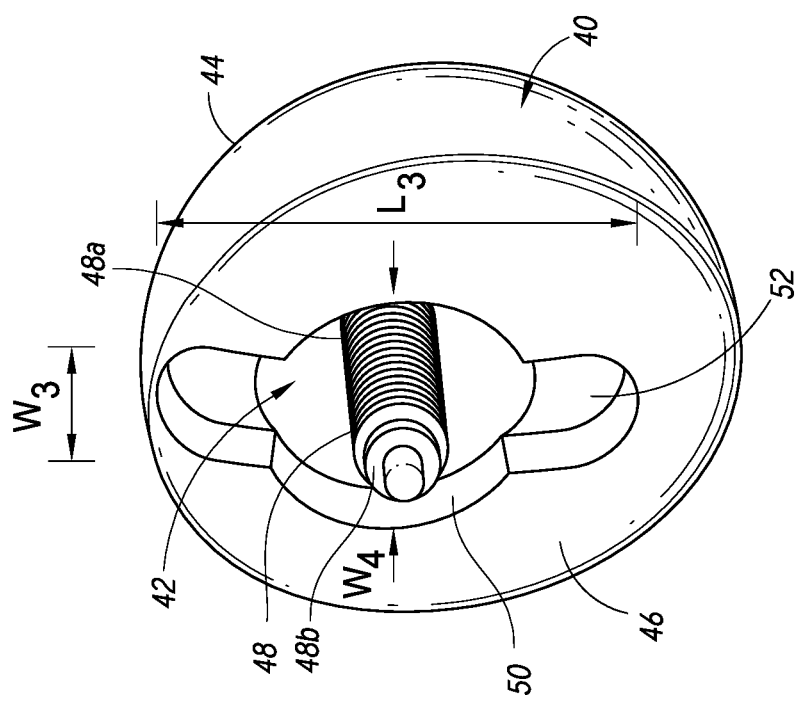
FIG. 2D illustrates an embodiment of a reverse component that can interface with the base plate shown in FIGS. 2A-2C.
Figure 2F:
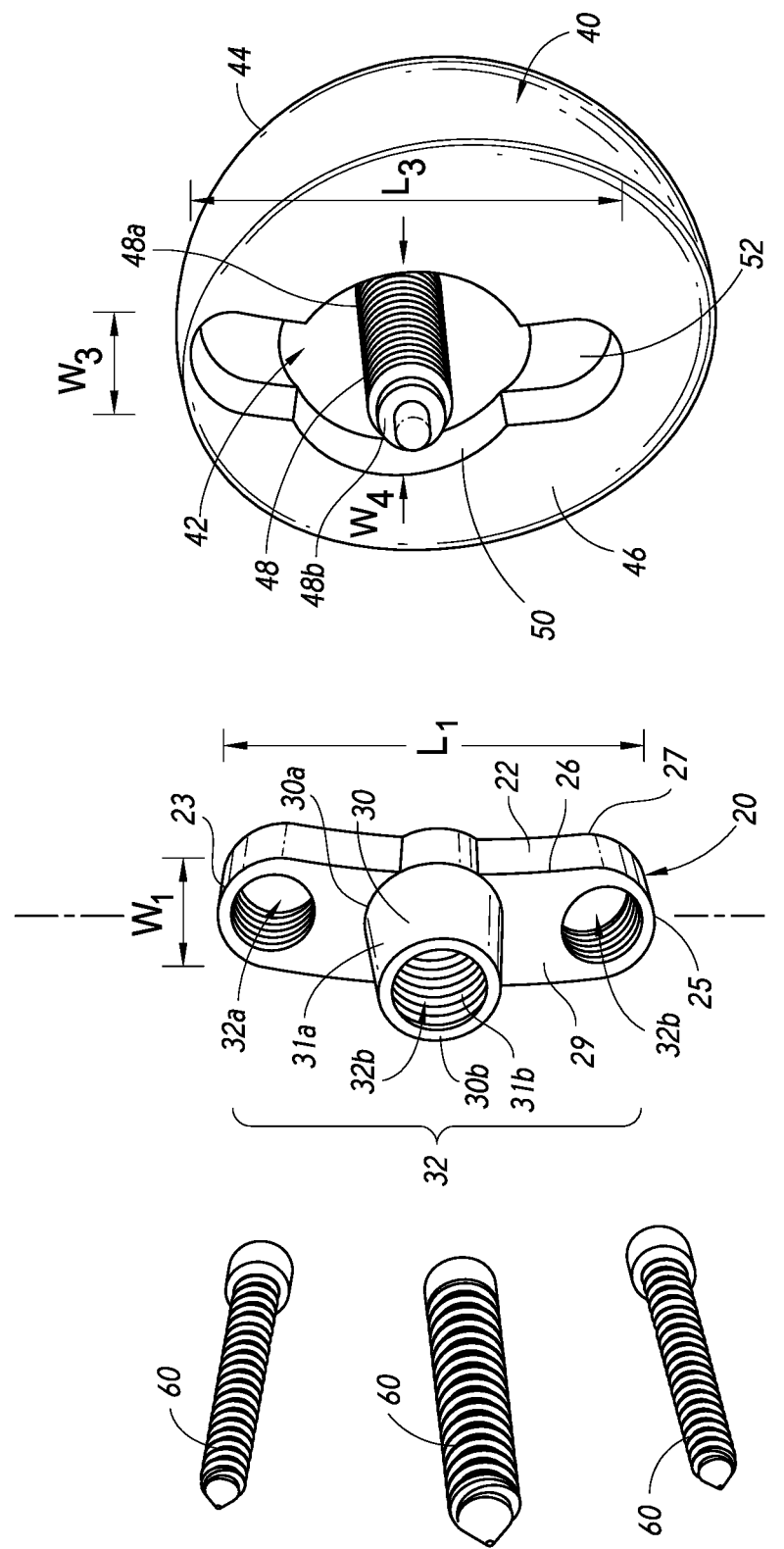
FIG. 2F illustrates an exploded view of the reverse glenoid implant shown in FIG. 2E.

As shown in FIGS. 2E and 2F, a reverse component 40 can interface with the base plate 20 shown in FIGS. 2A-2C to form the glenoid implant 1002. The reverse component 40 can include a medial surface 46 (or distal surface) and an articulating surface 44 configured to interface with a portion of a humeral component. The medial surface 46 can include a recessed portion 42 having a peripheral wall 50 and a medial-facing surface 52 (or distal-facing surface).

The recessed portion 42 can be eccentric with respect to the reverse component 40. For example, the recessed portion 42 can be closer to an inferior anatomic edge of the reverse component 40 than to a superior anatomic edge of the reverse component 40. The reverse component 40 can be placed more inferior on the glenoid surface than the glenoid component 6 to prevent scapular notching. The medial surface 46 of the reverse component 40 can be curved to fit the curve of the glenoid.

The recessed portion 42 can be shaped and sized to receive at least a partial thickness of the body 26. For instance, the recessed portion 42 can have a generally elongate shape. A $L_3$ of the recessed portion 42 can be substantially longer than a width $W_3$ of the body 26, e.g., the length $L_3$ can be at least about three times longer than the width $W_3$, at least about four times longer than the width $W_3$, or more. A width $W_4$ of a section of the recessed portion 42 surrounding the engagement structure 48 can be greater than the width $W_3$ at another section of the recessed portion 42. A thickness of the recessed portion 42 surrounding the engagement structure 48 can be greater than a thickness of the recessed portion 42 at other sections of the recessed portion 42.

The recessed portion 42 can be larger than the body 26, such a space remains between the recessed portion 8 and the body 26 when the implant 1002 is fully assembled (see FIG. 2E). For example, the lateral surface 27 of the body 26 can be spaced apart from the medial-facing surface 52 of the recessed portion 42 and/or the peripheral walls 22 of the body 26 can be spaced apart from the peripheral walls 50 of the recessed portion 42. When the implant 1002 is fully assembled, the medial surface 29 of the body 26 can be aligned or flush with the medial surface 46 of the reverse component 40 (See FIG. 2E). Although not shown, the space between the recessed portion 8 and the body 26 can be filled with a shock absorbing material, such as polymers and copolymers, including but not limited to silicone and polyurethane.

At least one engagement structure 48 (e.g., one, two, three, four, five or more engagement structures) can protrude from the medial-facing surface 52 of the recessed portion 42 and extend generally perpendicular to the length $L_3$ of the recessed portion 42. Each engagement structure 48 can be a peg, a barb, a screw, or other protruding structure, configured to be received by one of the openings 32 by a screw fit, snap fit, interference fit or otherwise. As shown in FIG. 2D, the reverse component 40 can include a single, engagement structure 48 configured to interface with the opening 32b and/or the support structure 30.

Each engagement structure 48 can include an outer wall portion that can be threaded to threadably engage of the openings 32. The outer wall portion can extend from a proximal portion 48a to a distal portion 48b of the engagement structure 48. A length of the engagement structure 48 can be greater than a thickness of the recessed portion 42, such that the distal portion 48b of the engagement structure 48 extends distally of the medial surface 46 of the reverse component 40. The distal portion 48b of each engagement structure 18 can be tapered to facilitate insertion of the engagement structure 18 into one of the openings 32 and/or the support structure 30.

Figure 3B:
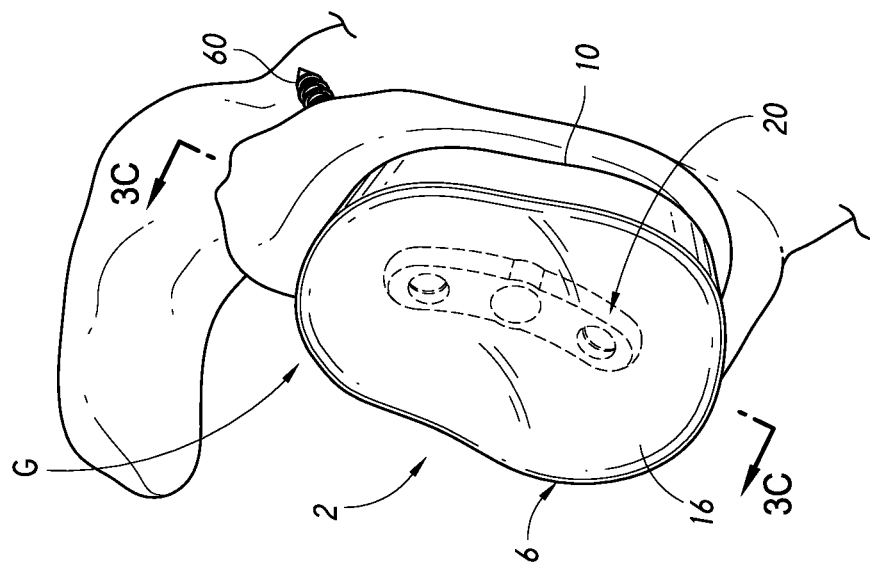
FIG. 3B illustrates a glenoid component secured to the base plate shown in FIG. 3A.
Figure 3A:
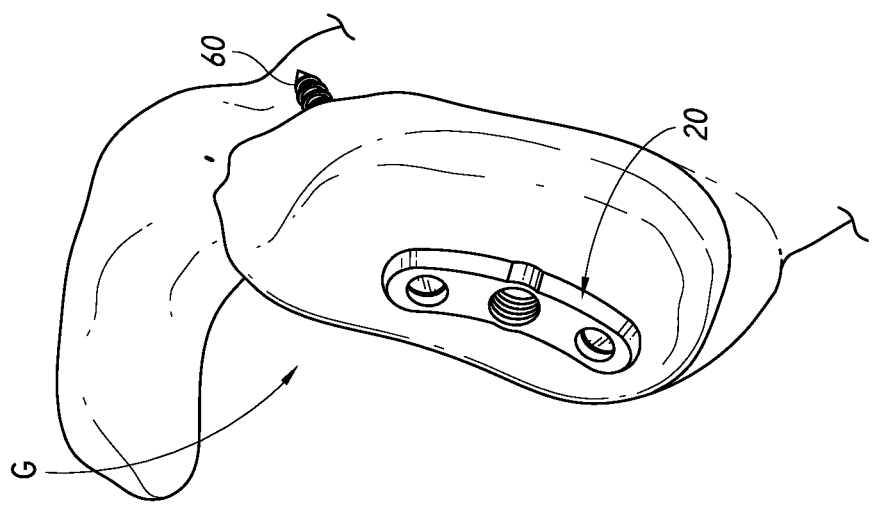
FIG. 3A illustrates a base plate secured to a glenoid.
Figure 3D:
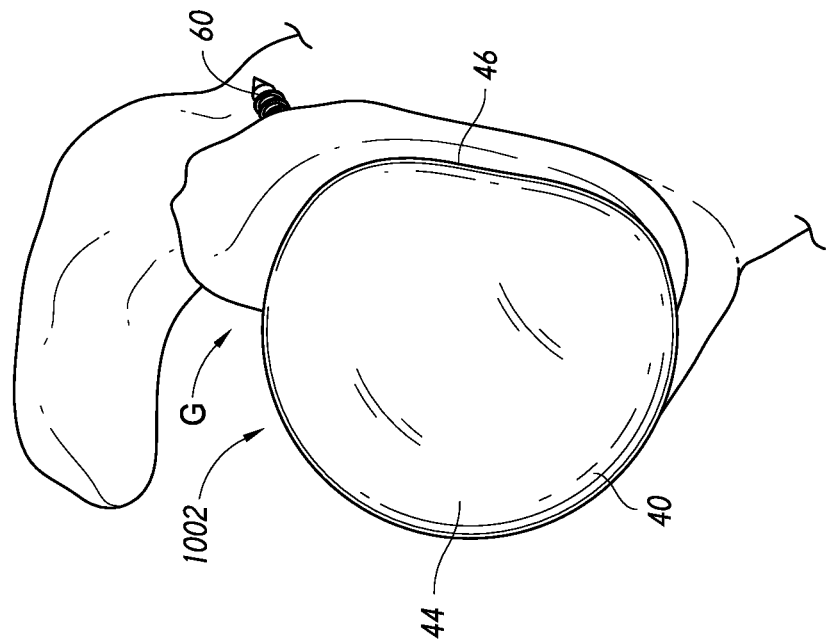
FIG. 3D illustrates a perspective view of the reverse glenoid implant of FIGS. 2D-2F secured to the glenoid.
Figure 3C:
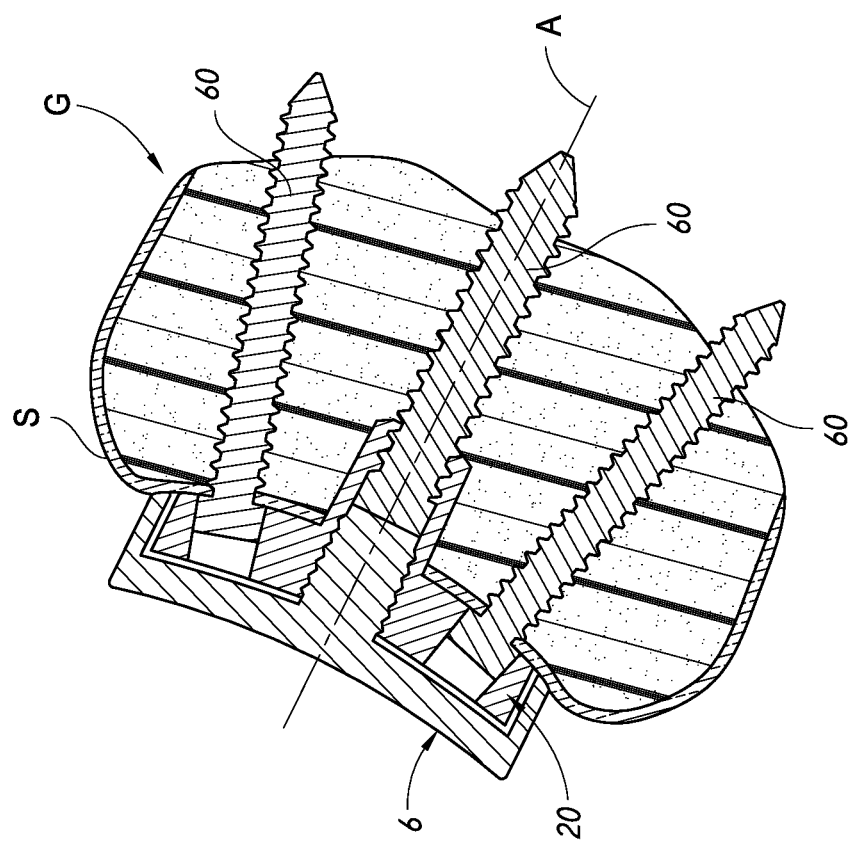
FIG. 3C illustrates a cross-section of the glenoid implant shown in FIG. 3B taken along line 3C-3C.

FIGS. 3A-3C illustrate the glenoid implant 2 secured to the glenoid G. As shown in FIG. 3A, the base plate 20 can be secured to the glenoid G with the length of the body 26 extending in a superior-inferior direction. After the base plate 20 has been secured to the glenoid G using one or more screws 60, the glenoid component 6 can be secured over the base plate 20 (see FIG. 3B). When the glenoid component 6 is coupled to the base plate 20, a peripheral edge of the glenoid component 6 can form an entire peripheral edge of the glenoid implant 2. That is to say, the entire peripheral edge exterior to the glenoid G (e.g., from the lateral surface 16 to the medial surface 10 of the glenoid implant) can be the glenoid component 6 wherein the base plate 20 is captured between the glenoid component 6 and the glenoid G.

As shown in FIG. 2B, the medial surface 29 of the body 26 can be substantially flush with the medial surface 10 of the glenoid component 6 when the glenoid implant 2 is assembled. In this configuration, the medial surface 10 of the glenoid component 6 and the medial surface 29 of the body 26 can be configured to abut the subchondral bone S. That is to say, at least a portion of each of the medial surface 10 of the glenoid component 6 and the medial surface 29 of the body 26 are in direct contact with the subchondral bone S. When the medial surface 29 of the body 26 is positioned on the subchondral bone S, a surgeon can lag one or more screws 60 into the subchondral bone S to achieve the desired compression and fix the base plate 20 to the glenoid G. Additionally, since the medial surface 29 of the body can be positioned on the subchondral bone S, it is unnecessary to mill or ream the glenoid G before inserting the glenoid implant 2.

FIG. 3D illustrates a perspective view of the glenoid implant 1002 secured to the glenoid G for use in a reverse shoulder arthroplasty. The glenoid implant 1002 includes the reverse component 40, baseplate 20, and screws 60. The reverse component 40 can be secured to the same base plate 20 shown in FIGS. 3A-3C. When the reverse component 40 is secured to the base plate 20, the medial surface 46 of the reverse component 40 can be configured to abut the subchondral bone S.

Multiple, Aligned Engagement Structures

FIGS. 4A-4E illustrate additional embodiments of the glenoid components. The glenoid components resemble or are identical to the glenoid components discussed above except as described below. Accordingly, numerals used to identify features of the glenoid components shown in FIGS. 2A-2E are incremented by a factor of one hundred (100) to identify like features of the glenoid components shown in FIGS. 4A-4E. Any component or step disclosed in any embodiment in this specification can be used in other embodiments.

The glenoid component 106 can include a plurality of engagement structures 118 (e.g., two, three, four, five, or more engagement structures). Each engagement structure 118 can be similar to the engagement structure 18 described above. The number of the engagement structures 118 can be the same as the number of openings 132 in the base plate 120. At least some of the engagement structures 118 can be aligned along a transverse axis of the glenoid component 106.

Figure 4D:
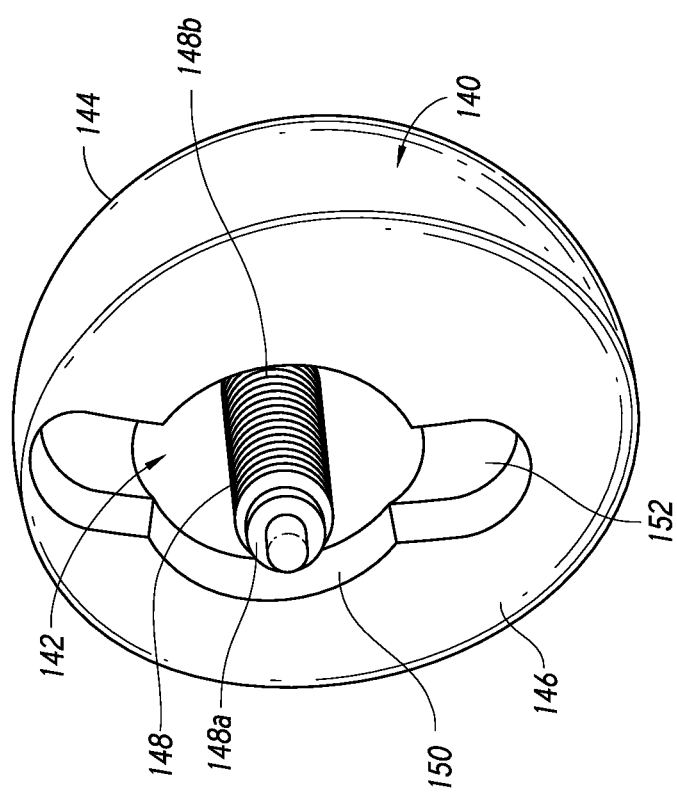
FIG. 4D illustrates a bottom perspective view of an embodiment of a reverse component that can interface with the base plate shown in FIG. 4C.
Figure 4E:
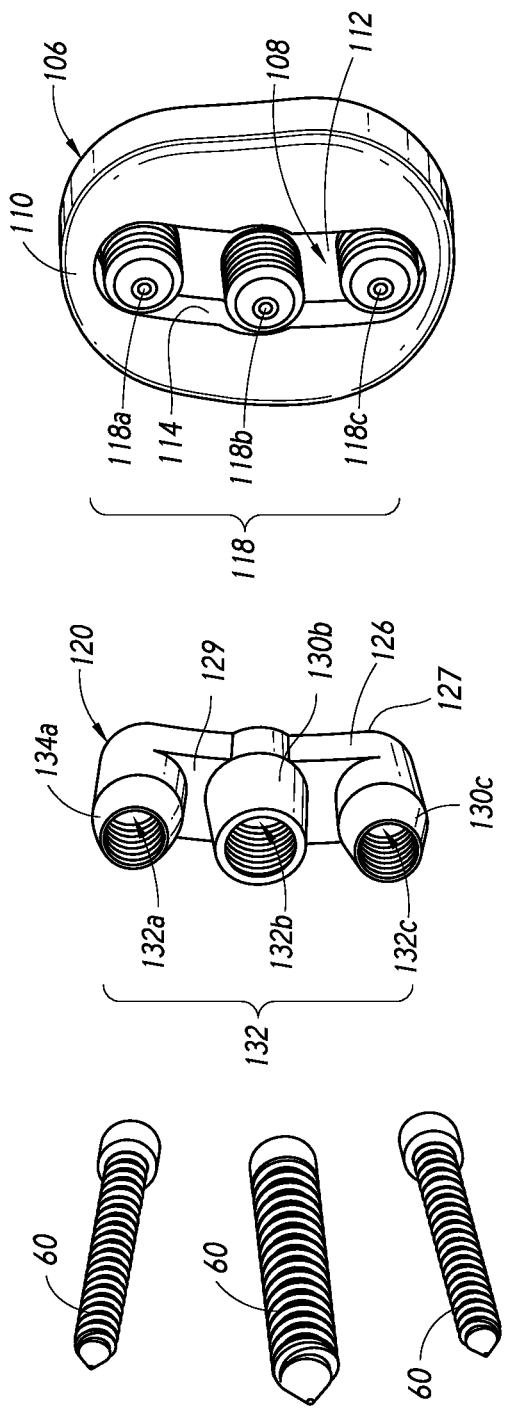
FIG. 4E illustrates an exploded view of the glenoid implant shown in FIG. 4A.

As shown in FIGS. 4A and 4E, the glenoid component 106 can include three engagement structures 118a, 118b, 118c aligned along the length of the recessed portion 108. Each engagement structure 118a, 118b, 118c can interface with the respective corresponding opening 132a, 132b, 132c. The central engagement structure 118b can be longer than the peripheral engagement structures 118a, 118c.

The base plate 120 can include a plurality of support structures 130a, 130b, 130c extending from the medial surface 129 of the body 126. Each of the support structures 130a, 130b, 130c can include features similar to the support structure 30 described above and be aligned with one of the openings 132a, 132b, 132c. Each support structure 130a, 130b, 130c can be configured to receive a corresponding engagement structure 118a, 118b, 118c. A length of the support structures 130a, 130b, 130c can be sufficient to accommodate a proximal portion of a screw 160 and the corresponding engagement structure 118a, 118b, 118c (see FIG. 4A). A central support structure 130b can be longer than peripheral support structures 130a, 130c FIG. 4D illustrates a reverse component 140 that can interface with the base plate 120 shown in FIG. 4C. As shown, the reverse component 140 can include a single engagement structure 148. However, in other embodiments, the reverse component 140 can include a plurality of engagement structures 148 (e.g., two, three, four, five, or more engagement structures). The number of engagement structures 148 can correspond to the number of openings 132 in the base plate 120. At least some of the engagement structures 148 can be aligned along a transverse axis of the reverse component 140. As one example, the reverse component 140 can include three engagement structure 148 aligned along the transverse axis of the reverse component 140.

Lateral Engagement Structures

FIGS. 5A-5F illustrate additional embodiments of the glenoid components. The glenoid components resemble or are identical to the glenoid components discussed above in many respects. Accordingly, numerals used to identify features of the glenoid components shown in FIGS. 4A-4E are incremented by a factor of 100 hundred (100) to identify like features of the glenoid components shown in FIGS. 5A-5F. This numbering convention generally applies to the remainder of the figures. Any component or step disclosed in any embodiment in this specification can be used in other embodiments.

Figure 5E:
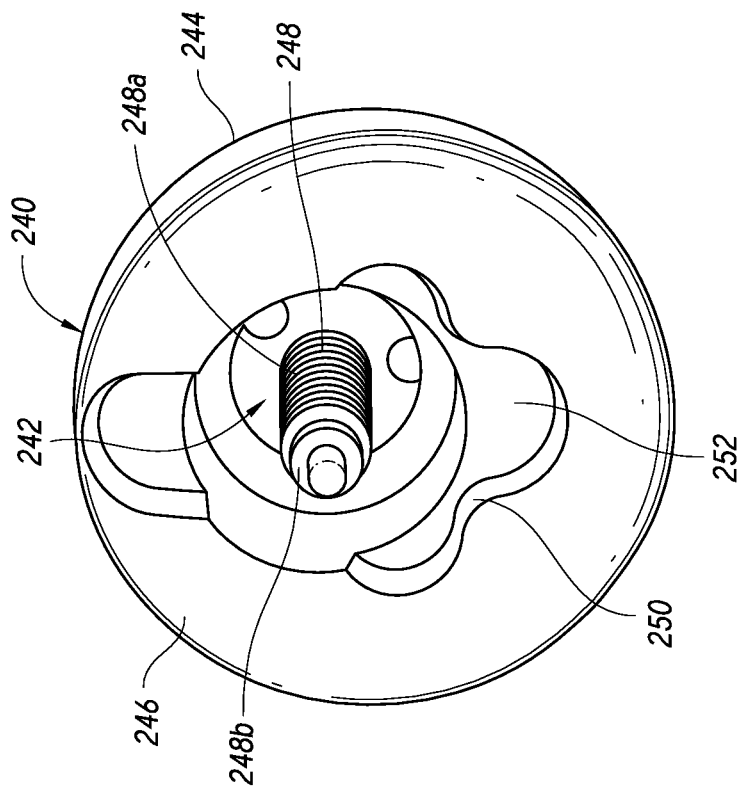
FIG. 5E illustrates an exploded view of the glenoid implant shown in FIG. 5A.

As shown in FIG. 5B, the glenoid component 206 can include a plurality of engagement structures 218 (e.g., two, three, four, five, or more engagement structures). Each engagement structure 218 can be similar to the engagement structure 18 described above. The number of engagement structures 218 can be the same as the number of openings 232 in the base plate 220 (see FIG. 5E). At least some of the engagement structures 218 can be aligned along a transverse axis of the glenoid component 206. For example, at least three engagement structures 218a, 218b, 218c can be aligned along the transverse axis of the glenoid component 206. Additional engagement structures 218d, 218e can be laterally displaced from the aligned engagement structures 218a, 218b, 218c and/or from a central transverse axis A (see FIG. 5B). The laterally displaced engagement structures 218d, 218e can be positioned such that the arrangement of engagement structures 218 is symmetrical about an axis extending through the aligned engagement structures 218a, 218b, 218c. The laterally displaced engagement structures 218d, 218e can be offset from the aligned engagement structures 218a, 218b 218c, for example, the laterally displaced engagement structures 218d, 218e can be positioned between the engagement structures 218b, 218c.

Figure 5C:
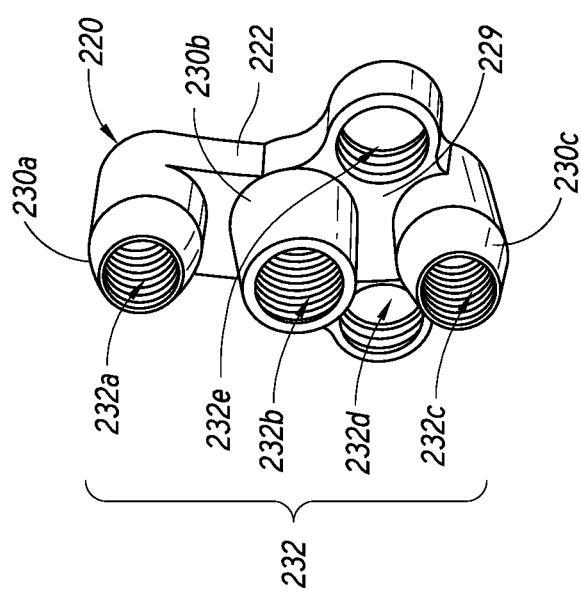
FIG. 5C illustrates a bottom perspective view of the base plate shown in FIG. 4A.
Figure 5D:
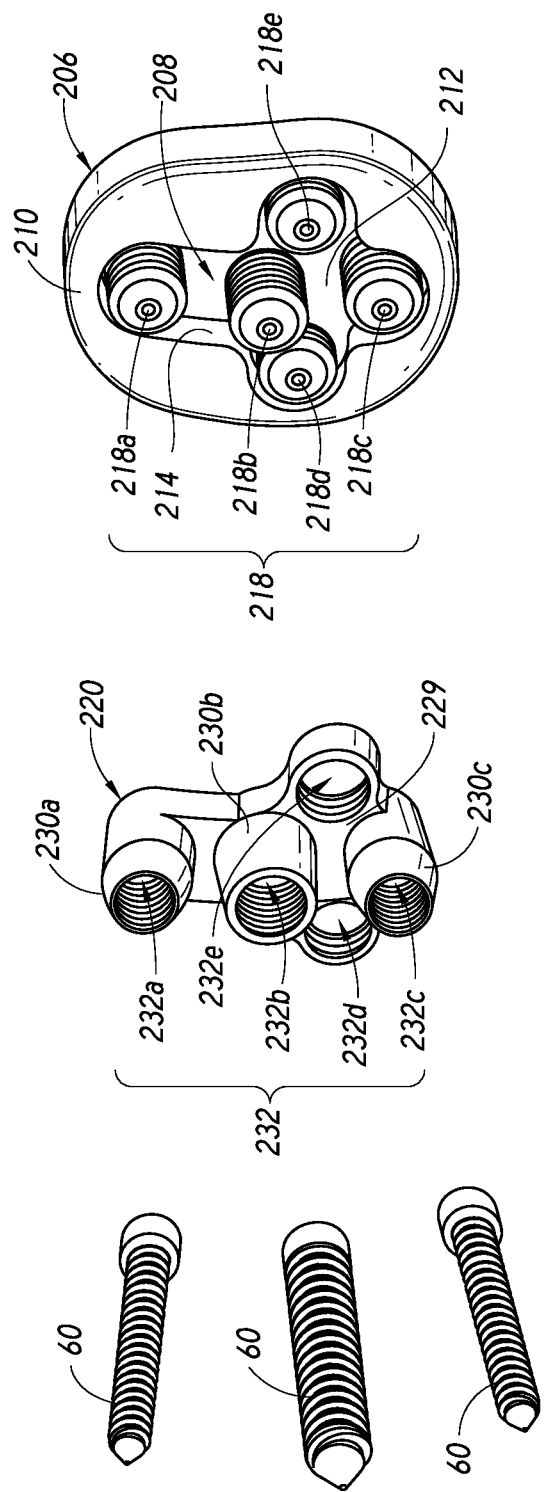
FIG. 5D illustrates a bottom perspective view of another embodiment of a reverse component that can interface with the base plate shown in FIG. 4C.

As shown in FIG. 5C, the base plate 220 can include laterally displaced openings 232d, 232e to accommodate the laterally displaced engagement structures 218d, 218e. For example, the base plate 220 can include three openings 232a, 232b, 232c aligned along the transverse axis of the base plate 220 and two openings 232d, 232e displaced from the aligned openings 232a, 232b, 232c. The laterally displaced openings 232d, 232e can be positioned such that the arrangement of openings 232 is symmetrical about the aligned openings 232a, 232b, 232c. The laterally displaced openings 232d, 232e can be offset from the aligned openings 232a, 232b, 232c, for example, the laterally displaced openings 232d, 232e can be positioned between the engagement structures 232b, 232c.

The base plate 220 can include a plurality of support structures 230a, 230b, 230c extending from the medial surface 229 of the body 226. Each of the support structures 230a, 230b, 230c can include features similar to the support structure 30 described above and can be aligned with one of the openings 232. At least some of the openings 232 can provide access to a corresponding support structure 230a, 230b, 230c. As shown in FIG. 5C, the support structures 230a, 230b, 230c can extend from the aligned openings 232a, 232b, 232c, but not the laterally displaced openings 232d, 232e. However, other quantities of support structures can be imagined, for example, the number of support structures can be the same as the number of openings.

FIG. 5E illustrates a reverse component 240 that can interface with the base plate 220 shown in FIG. 5C. The reverse component 240 can include a recessed portion 242 that can be sized to accommodate the base plate 230, including the laterally displaced openings 218e, 218d.

Figure 5F:
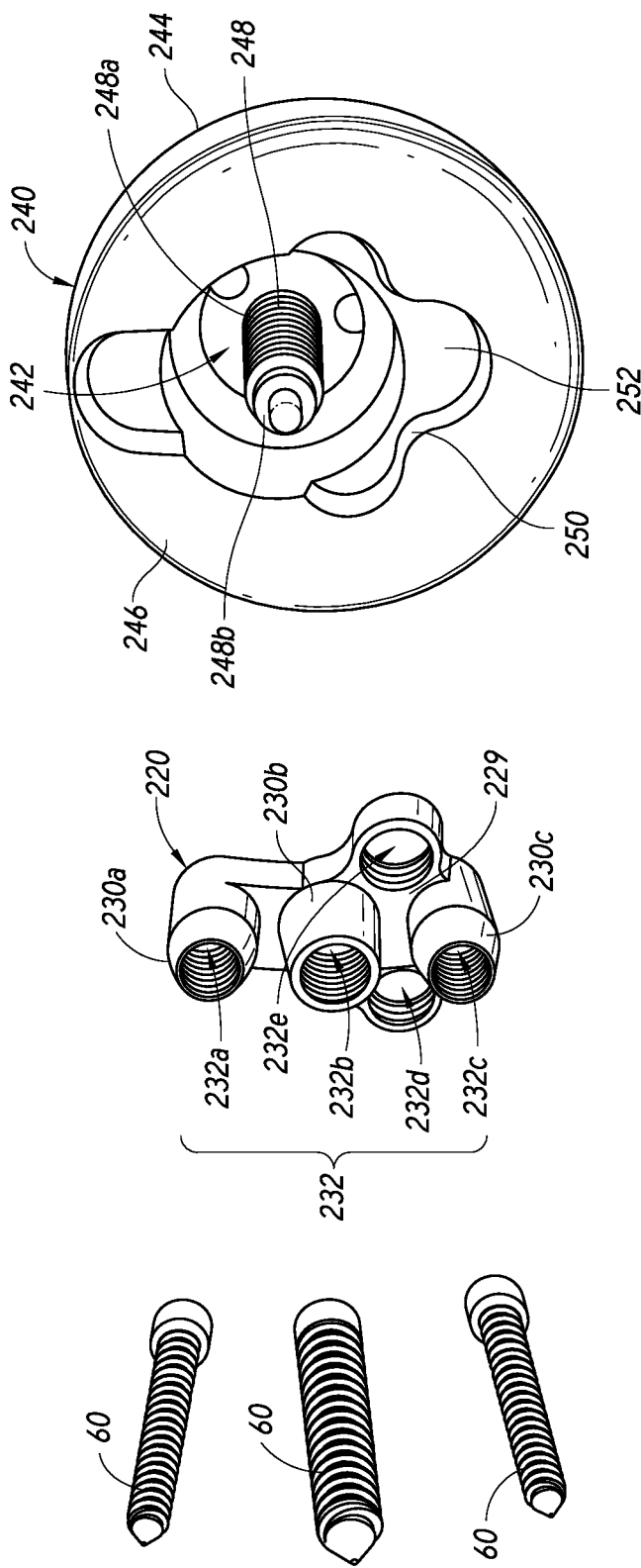
FIG. 5F illustrates an exploded view of a reverse glenoid implant with the reverse component shown in FIG. 5D.

As shown in FIGS. 5E and 5F, the reverse component 240 can include a single engagement structure 248 similar to engagement structure 48. However, in other embodiments, the reverse component 240 can include a plurality of engagement structures 248 (e.g., two, three, four, five, or more engagement structures). The number of engagement structures 248 can correspond to the number of openings 232 and/or support structures 230a, 230b, 230c in the base plate 220. At least some of the engagement structures 248 can be aligned along a transverse axis of the reverse component 240, similar to the engagement structures 218a, 218b, 218c in FIG. 5B. As one example, the reverse component 240 can include three engagement structures 248 aligned along the transverse axis of the reverse component 240. As another example, a subset of the engagement structures 248 can be aligned along the transverse axis of the reverse component 240, while additional engagement structures 248 can be laterally displaced from the aligned engagement structures 248, e.g., to correspond with the arrangement of openings 232 in the base plate 220. Accordingly, the section of the recessed portion 248 accommodating the laterally displaced openings 232d, 232e can be wider than a remaining section of the recessed portion 248.

Method of Implantation

Referring back to the glenoid implants 2, 1002 shown in FIGS. 3A-3D, in use, the base plate 20 can be secured to the glenoid G by inserting a support structure 30 of the base plate 20 into a subchondral bone portion S and positioning a medial surface 29 of the body 26 of the base plate 20 on the subchondral bone surface S. As shown in FIG. 3A, the body 26 can be positioned such that the length of the body 26 extends in the superior-inferior direction. A screw 60 can be advanced through at least one of the plurality of openings 32 of the body 26 and into the subchondral bone S.

The glenoid component 6 can be secured to the base plate 20 by advancing the recessed portion 8 of the glenoid component 6 over the body 26 of the base plate 20 and inserting an engagement member 18 of the glenoid component 6 into a corresponding opening of the plurality of openings 32 (e.g., the opening 32b extending through the support structure 30). A proximal portion of a screw 60 and the engagement structure 18 can be positioned in the support structure 30. A space is maintained between the lateral surface 27 of the body 26 and the medial-facing surface 12 of the recessed portion 8 and/or the peripheral wall 22 of the body 26 and the peripheral wall 14 of the recessed portion 8. After the glenoid component 6 is advanced over the base plate 30, the medial 10 of the glenoid component 6 can abut the subchondral bone S.

It may become necessary to remove the glenoid component 6 from the base plate, for example, if the glenoid implant 2 begins to wear or the bone further deteriorates. The reverse component 40 can be secured to the base plate 20 to form the glenoid implant 1002.

Although this method is described in the context of the glenoid components shown in FIGS. 3A-3D, a similar method can be used to implant glenoid implants 102 and 202.

TERMINOLOGY

Although certain embodiments have been described herein with respect to an anatomic component or a reverse component, the implants and methods described herein can interchangeably use any articular component, including the anatomic and reverse components described herein, as the context may dictate.

As used herein, the relative terms "proximal" and "distal" shall be defined from the perspective of the implant. Thus, proximal refers to the direction of the articular component and distal refers to the direction of the base plate when the implant is assembled.

Note that the terms "first" and "second" articular components can be used interchangeably and to refer to the anatomic components or the reverse components. Accordingly, the "first" and "second" openings can be used interchangeably and to refer to any one of the openings in the baseplate.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

The terms "approximately," "about," and "substantially" as used herein represent an amount close to the stated amount that still performs a desired function or achieves a desired result. For example, the terms "approximately," "about," and "substantially" may refer to an amount that is within less than 10% of the stated amount, as the context may dictate. As an example, in certain embodiments, the term "generally perpendicular" refers to a value, amount, or characteristic that departs from exactly perpendicular by less than about 10 degrees.

Although certain embodiments and examples have been described herein, it will be understood by those skilled in the art that many aspects of the glenoid implants shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

Any methods disclosed herein need not be performed in the order recited. The methods disclosed herein include certain actions taken by a practitioner; however, they can also include any third-party instruction of those actions, either expressly or by implication. For example, actions such as "inserting a base plate into a glenoid cavity" include "instructing insertion of a base plate into a glenoid cavity."

EXAMPLE EMBODIMENTS

The following example embodiments identify some possible permutations of combinations of features disclosed herein, although other permutations of combinations of features are also possible.

1. A glenoid implant comprising:
 a base plate comprising a body and at least one support structure extending from a distal surface of the body, the body comprising a plurality of openings; and
 an articular component configured to removably couple to the base plate, the articular component comprising:
  a recessed portion configured to at least partially receive the body of the base plate; and
  at least one engagement structure protruding from a distal facing surface of the recessed portion, each of the at least one engagement structure corresponding to one of the plurality of openings in the body;
 wherein a proximal surface of the base plate is spaced apart from the distal facing surface of the recessed portion when the articular component is coupled to the base plate.

2. The implant of Embodiment 1, further comprising a shock absorbing material between the proximal surface of the base plate and the distal facing surface of the recessed portion.

3. The implant of Embodiment 2, wherein the shock absorbing material is selected from the group consisting of silicone and polyurethane.

4. The implant of any one of Embodiments 1 to 3, wherein the recessed portion is eccentric with respect to the articular component.

5. The implant of any one of Embodiments 1 to 4, wherein the recessed portion is closer to an inferior anatomic edge of the articular component than a superior anatomic edge of the articular component.

6. The implant of any one Embodiments 1 to 5, wherein a peripheral edge of the articular component forms an entire peripheral edge of the implant when the articular component is coupled to the base plate.

7. The implant of any one of Embodiments 1 to 6, wherein sidewalls of the recessed portion are spaced apart from side walls of the body when the articular component is coupled to the base plate.

8. The implant of any one of Embodiments 1 to 7, wherein the plurality of openings comprises a first opening, a second opening, and a third opening, and wherein the first opening, the second opening, and the third opening are axially aligned along a transverse axis of the body.

9. The implant of Embodiment 7, further comprising a fourth opening laterally displaced from the axially aligned openings.

10. The implant of any one of Embodiments 1 to 9, wherein the at least one support structure comprises a plurality of support structures, each of the plurality of openings of the body providing access to a corresponding support structure.

11. The implant of Embodiment 10, wherein each of the plurality of support structures corresponds to one of the at least one engagement structures.

12. The implant of any one of Embodiments 1 to 11, wherein the plurality of openings are configured for insertion of at least one screw into at least one of the plurality of openings.

13. The implant of any one of Embodiments 1 to 12, wherein the articular component is a reverse component or a glenoid component.

14. A glenoid implant comprising:
a base plate comprising a body and a support structure extending from a distal surface of the body, a length of the body being greater than a width of the body, the body comprising a plurality of openings, the base plate comprising a metal; and
an articular component comprising a polymer, the articular component configured to removably couple to the base plate, the articular component comprising:
a recessed portion configured to at least partially receive the body of the base plate; and
at least one engagement structure protruding from a distal facing surface of the recessed portion, each of the at least one engagement structure corresponding to one of the plurality of openings in the body,
wherein a distal face of the articular component surrounding the recessed portion is configured to abut the subchondral bone.

15. The glenoid implant of Embodiment 14, wherein the distal surface of the body is configured to abut the subchondral bone.

16. The glenoid implant of Embodiment 14 or 15, wherein the base plate is configured such that at least one screw can be screwed through at least one of the plurality of openings and into the subchondral bone.

17. A method of implanting a glenoid implant in a glenoid cavity, the method comprising:
inserting a base plate into a glenoid cavity such that a support structure of the base plate is inserted into a subchondral bone portion and a body of the base plate is positioned thereon a subchondral bone surface, the body comprising a plurality of openings;
advancing a screw through one of the plurality of openings and into the subchondral bone; and
securing a first articular component to the base plate such that a recessed portion of the first articular component is advanced over the body of the base plate and an engagement member of the first articular component is inserted into a corresponding opening of the plurality of openings.

18. The method of Embodiment 17, wherein securing the first articular component to the base plate comprises maintaining a space between a proximal surface of the body and a distal facing surface of the recessed portion.

19. The method of Embodiment 17 or 18, wherein securing the first articular component to the base plate comprises positioning a distal face of the first articular component to abut the subchondral bone.

20. The method of any one of Embodiments 17 to 19, wherein securing the first articular component comprises inserting the engagement member into said one of the plurality of openings housing the screw.

21. The method of any one of Embodiments 17 to 20, further comprising advancing each of a plurality of screws into each of the plurality of openings.

22. The method of any one of Embodiments 17 to 21, further comprising:
removing the first articular component from the base plate; and
securing a second articular component to the base plate, wherein the first articular component is a glenoid component and the second articular component is a reverse component.

23. A glenoid system comprising:
a base plate comprising a body and a support structure extending from a distal surface of the body, the body comprising a plurality of openings; and
an glenoid component configured to removably couple to the base plate, the glenoid component comprising an anatomical recessed portion configured to at least partially receive the body of the base plate, a proximal surface of the base plate being spaced apart from a distal facing surface of the anatomical recessed portion when the glenoid component is coupled to the base plate,
a reverse component configured to removably couple to the base plate, the reverse component comprising a reverse recessed portion configured to at least partially receive the body of the base plate, the proximal surface of the base plate being spaced apart from a distal facing surface of the reverse recessed portion when the reverse component is coupled to the base plate.

The following is claimed:

1. A glenoid implant comprising:
a base plate comprising a body having a proximal surface, a distal surface, and an outer peripheral wall extending from the proximal surface to the distal surface, the body comprising a plurality of openings; and
an articular component configured to removably couple to the base plate, the articular component comprising:
an articular surface;
a distal face;
a recessed portion recessed from the distal face of the articular component, the recessed portion configured to at least partially receive the body of the base plate, the recessed portion comprising a distal facing surface and a peripheral wall extending from the distal facing surface; and
at least one engagement structure protruding from the distal facing surface of the recessed portion, each of the at least one the engagement structure corresponding to one of the plurality of openings in the body;
the articular component having an expanse of material extending continuously from the articular surface to the recessed portion, the expanse of material being uninterrupted by an interface with any other components between the articular surface and the recessed portion;
wherein there is an unfilled space between the peripheral wall of the recessed portion and the outer peripheral wall of the body when the articular component is coupled to the base plate, the unfilled space free of any other components when the body of the base plate is received in the recessed portion of the articular component, and wherein when assembled, the distal surface of the body is aligned with the distal face of the articular component.

2. The implant of claim 1, wherein the recessed portion is eccentric with respect to the articular component.

3. The implant of claim 1, wherein the recessed portion is closer to an inferior anatomic edge of the articular component than a superior anatomic edge of the articular component.

4. The implant of claim 1, wherein a peripheral edge of the articular component forms an entire peripheral edge of the implant when the articular component is coupled to the base plate.

5. The implant of claim 1, wherein the plurality of openings comprises a first opening, a second opening, and a third opening, and wherein the first opening, the second opening, and the third opening are axially aligned along the body.

6. The implant of claim 5, further comprising a fourth opening laterally displaced from the axially aligned openings.

7. The implant of claim 1, wherein the plurality of openings are configured for insertion of at least one screw into at least one of the plurality of openings.

8. The implant of claim 1, wherein the articular component is a reverse component or a glenoid component.

9. The glenoid implant of claim 1, wherein the base plate comprises at least one support structure extending from the distal surface of the body.

10. The implant of claim 9, wherein the at least one support structure comprises a plurality of support structures, each of the plurality of openings of the body providing access to a corresponding support structure.

11. The implant of claim 10, wherein each of the plurality of support structures corresponds to one of the at least one engagement structures.

12. A glenoid implant comprising:
a base plate comprising a body, the body comprising a plurality of openings; and
a polymeric articular component configured to removably couple to the base plate, the articular component comprising:
an articular surface;
a recess opposite the articular surface, the recess configured to at least partially receive the body of the base plate; and
at least one engagement structure protruding from the recess, each of the at least one engagement structure corresponding to one of the plurality of openings in the body, the articular component having an expanse of polymeric material extending continuously from the articular surface to the recess, the expanse of material being uninterrupted by an interface with any other components between the articular surface and the recess;

wherein there is an unfilled space between a peripheral wall defining the recess and an outer peripheral wall of the body when the articular component is coupled to the base plate, the unfilled space free of any other components when the body of the base plate is received in the recess of the articular component, and wherein a distal face of the articular component surrounding the recess and a distal surface of the body are configured to abut the subchondral bone when implanted.

13. The glenoid implant of claim 12, wherein the base plate is configured such that at least one screw can be screwed through at least one of the plurality of openings and into the subchondral bone.

14. The glenoid implant of claim 12, wherein the base plate comprises a metal.

15. The glenoid implant of claim 12, wherein a length of the distal surface of the body is greater than a width of the distal surface of body.

16. The glenoid implant of claim 12, wherein a support structure extends from the distal surface of the body.

17. A glenoid system comprising:
the glenoid implant of claim 1, wherein the articular component is an anatomical component comprising a concave articular surface; and
a reverse component configured to removably couple to the base plate, the reverse component comprising a second distal face and a second recessed portion configured to at least partially receive the body of the base plate, the second recessed portion recessed from the second distal face of the reverse component, the second recessed portion comprising a second distal facing surface and a second peripheral wall extending from the second distal facing surface, the proximal surface of the body being spaced apart from the second distal facing surface of the reverse recessed portion when the reverse component is coupled to the base plate,
wherein the second peripheral wall of the second recessed portion is spaced apart from and radially outward of the outer peripheral wall of the body when the articular component is coupled to the base plate, and
wherein when assembled, the distal surface of the body is aligned with the second distal face of the reverse component.

* * * * *

UNITED STATES PATENT AND TRADEMARK OFFICE
CERTIFICATE OF CORRECTION

PATENT NO. : 10,722,374 B2
APPLICATION NO. : 15/058045
DATED : July 28, 2020
INVENTOR(S) : Brian C. Hodorek Page 1 of 1

It is certified that error appears in the above-identified patent and that said Letters Patent is hereby corrected as shown below:

In Column 15, Line 29, Claim 9, delete "The glenoid implant of claim 1," and insert --The implant of claim 1--.

Signed and Sealed this
Sixth Day of October, 2020

Andrei Iancu
*Director of the United States Patent and Trademark Office*